United States Patent
Li et al.

(10) Patent No.: US 11,879,336 B2
(45) Date of Patent: Jan. 23, 2024

(54) MONITORING DEVICE AND METHOD FOR DYNAMIC DEVELOPMENT OF OVERBURDEN MINING SEPARATED BED

(71) Applicant: CHINA UNIVERSITY OF MINING AND TECHNOLOGY, Xuzhou (CN)

(72) Inventors: Wenping Li, Xuzhou (CN); Weichi Chen, Xuzhou (CN); Qiqing Wang, Xuzhou (CN); Jianghui He, Xuzhou (CN); Wei Qiao, Xuzhou (CN); Liangning Li, Xuzhou (CN); Yuru Yang, Xuzhou (CN)

(73) Assignee: CHINA UNIVERSITY OF MINING AND TECHNOLOGY, Xuzhou (CN)

( * ) Notice: Subject to any disclaimer, the term of this patent is extended or adjusted under 35 U.S.C. 154(b) by 395 days.

(21) Appl. No.: 17/411,061

(22) Filed: Aug. 25, 2021

(65) Prior Publication Data

US 2022/0290563 A1    Sep. 15, 2022

Related U.S. Application Data

(63) Continuation of application No. PCT/CN2021/095931, filed on May 26, 2021.

(30) Foreign Application Priority Data

Mar. 9, 2021 (CN) .......................... 202110253756.7
Mar. 9, 2021 (CN) .......................... 202110253757.1

(51) Int. Cl.
*E21C 39/00* (2006.01)
*G01N 33/24* (2006.01)
*E21B 49/00* (2006.01)

(52) U.S. Cl.
CPC .............. *E21C 39/00* (2013.01); *E21B 49/00* (2013.01); *G01N 33/24* (2013.01)

(58) Field of Classification Search
CPC .......... E21C 39/00; E21B 49/00; G01N 33/24
See application file for complete search history.

(56) References Cited

FOREIGN PATENT DOCUMENTS

| CN | 105136110 A | * 12/2015 | ............... G01C 5/00 |
| CN | 208996032 U | 6/2019 | |

(Continued)

OTHER PUBLICATIONS

Xin Lin, et al., Measurement analysis of overlying strata movement and surface subsidence by UCG strip mining, Journal of Mining & Safety Engineering, 2014, pp. 447-455, vol. 31, No. 3.

(Continued)

*Primary Examiner* — Ryan D Walsh
(74) *Attorney, Agent, or Firm* — Bayramoglu Law Offices LLC (57) ABSTRACT

A monitoring device and a monitoring method for dynamic development of an overburden mining separated bed are provided. The monitoring device includes a settlement magnetic ring assembly and a mounting conduit. The settlement magnetic ring assembly includes an anchor strap assembly, a magnetic induction iron ring and a magnetic ring sleeve sleeved outside the magnetic induction iron ring. The anchor strap assembly is arranged at the outer circumference of the magnetic ring sleeve and has a contraction state and an expansion state. The anchor strap assembly in the contraction state can move in a monitoring hole, and at least two fixing points at different heights are formed in the anchor strap assembly in the expansion state and the wall of the monitoring hole in a vertical direction. Two ends of the mounting conduit are connected to a drill rod and the magnetic ring sleeve respectively.

20 Claims, 5 Drawing Sheets

(56) References Cited

FOREIGN PATENT DOCUMENTS

| CN | 110207653 A | 9/2019 | |
|---|---|---|---|
| CN | 110469353 A | 11/2019 | |
| KR | 101185808 B1 | 10/2012 | |
| WO | WO-2018054107 A1 * | 3/2018 | ............... E02D 1/02 |

OTHER PUBLICATIONS

Detailed Rules of Coal Mine Water Control, 2018, pp. 1-72, National Mine Safety Administration.

* cited by examiner

MONITORING DEVICE AND METHOD FOR DYNAMIC DEVELOPMENT OF OVERBURDEN MINING SEPARATED BED

CROSS REFERENCE TO THE RELATED APPLICATIONS

This application is the continuation application of International Application No. PCT/CN2021/095931, filed on May 26, 2021, which is based upon and claims priority to Chinese Patent Applications No. 202110253757.1 and No. 202110253756.7, both filed on Mar. 9, 2021, the entire contents of which are incorporated herein by reference.

TECHNICAL FIELD

The present invention belongs to the technical field of coal mine separated bed settlement monitoring devices, in particular to a monitoring device and method for dynamic development of an overburden mining separated bed.

BACKGROUND

Differences in lithology and thickness of strata may be caused due to different deposition times and depositional environments. When a coal bed is mined, inconsistent settlement deformations of various strata may be caused due to the damage to stress of overburden primary rocks, and thus a bed-separation space is formed between strata. On one hand, under the effect of negative pressure, a great quantity of water resources in a water-bearing stratum of the overburden accumulate into a separated bed cavity; and when the scale develops to a certain degree, an instantaneous separated bed water inrush accident may happen, which threatens safety mining of a working face of a mine. On the other hand, closing of the overburden bed-separation space may cause ground depression to form a settling pit with ponding, and the surface soil environment is changed, thereby threatening the surface ecology and the stability of a building. When a bed-separation space develops to the largest degree, surface grouting is an effective method for preventing and controlling separated bed water inrush and ground settlement; and relatively low prevention and control efficiency may be caused by premature (separated bed development is incomplete) or too late (the separated bed starts to close) grouting. Therefore, monitoring of dynamic development of the overburden separated bed is very important for preventing and controlling of separated bed water inrush and treating ground settlement.

In monitoring of soil layer settlement for construction projects of subways, bridges, foundation pits and the like, a magnetic ring type layered settlement gauge is employed for monitoring, which comprises a settlement pipe, a settlement magnetic ring and a magnetic induction probe. During monitoring, the settlement magnetic ring is sleeved on the settlement pipe and then is put down into the monitoring hole, and a sinking amount of a soil layer is judged according to the position of the settlement magnetic ring. However, the existing settlement magnetic ring cannot be directly applied to layered settlement monitoring of a rock stratum for the following reasons: (1) a layered settlement monitoring hole of the rock stratum is deeply buried and the number of the used settlement pipes is large; the existing settlement pipe connecting technology is small in bearing; the settlement pipe may be broken at the upper part during deep hole mounting, causing failure in mounting; (2) before an anchoring claw of the settlement magnetic ring bounces off, the settlement magnetic ring produces displacement under the effect of dead weight, causing an inaccurate mounting position, and the mounting position cannot be secondarily adjusted after recovery of the settlement magnetic ring; (3) the hardness of the rock is far stronger than that of the soil body, and wall grasping force of the existing settlement magnetic ring is weak, so that the existing settlement magnetic ring cannot be fixed to the rock wall of the monitoring hole for a long time, a monitoring depth is changed, and the accuracy of a monitoring result is influenced; and (4) a gap between one settlement pipe and the settlement magnetic ring is small, which limits a measuring span of the settlement magnetic ring; the settlement magnetic ring cannot freely move if the gap is blocked by rock debris or soil grains; and thus the measurement accuracy is influenced.

SUMMARY

In view of the above analysis, the present invention aims to provide a monitoring device and method for dynamic development of an overburden mining separated bed and solve one or more of the problems that an existing monitoring device cannot be adjusted in mounting position again after being mounted, recovery without damages for secondary mounting cannot achieved, and the existing monitoring device needs to be mounted in place at one time, so that the requirement for the mounting accuracy is very high, the construction difficulty is large, and the cost is high due to the incapability of reutilization; and in addition, the monitoring device cannot be stably fixed to the rock wall of a monitoring hole for a long time, and a change of a monitoring position causes adverse effect on the accuracy of a monitoring result.

A purpose of the present invention is implemented as follows:

In the first aspect, provided is a monitoring device for dynamic development of the overburden mining separated bed, comprising:

a settlement magnetic ring assembly, comprising an anchor strap assembly, a magnetic induction iron ring and a magnetic ring sleeve sleeved outside the magnetic induction iron ring, wherein the anchor strap assembly is arranged at the outer circumference of the magnetic ring sleeve and has a contraction state and an expansion state, the anchor strap assembly in the contraction state can move in a monitoring hole, and at least two fixing points at different heights are formed in the anchor strap assembly (7-3) in the expansion state and the wall of the monitoring hole in a vertical direction; and a mounting conduit, the two ends of which are connected with a drill rod and the magnetic ring sleeve respectively, the anchor strap assembly is in the contraction state or the expansion state by matching the drill rod with the mounting conduit to achieve mounting and recovery of the settlement magnetic ring assembly.

Further, the anchor strap assembly comprises long wall anchoring claws and hoop pieces; the first end of each long wall anchoring claw is connected to the outer circumference of the magnetic ring sleeve through a shaft, and the second end of each long wall anchoring claw is a claw end for the need of being embedded into the wall of the monitoring hole in the expansion state; and the lower end of each hoop piece is fixed to the magnetic ring sleeve, the upper end is provided with a turnover end in a shape of a horn mouth, and each turnover end is connected with the claw end of the corresponding long wall anchoring claw through a connection wire.

Further, the hoop pieces and the long wall anchoring claws are arranged in groups, and the number of the hoop pieces is at least 2 and are uniformly arranged on the outer circumference of the upper end of the magnetic ring sleeve.

Further, rotation spaces for the long wall anchoring claws to rotate around the shafts are formed in the outer sides of the hoop pieces respectively and are internally provided with elastomers respectively.

Further, each elastomer is an elastic rubber ring, each elastic rubber ring is at least partially sleeved on the magnetic ring sleeve; or each elastomer is a limiting spring, the first end of each limiting spring is connected to the corresponding long wall anchoring claw, and the second end of each limiting spring is connected to the outer circumference of the upper part of the magnetic ring sleeve or the lower part of the corresponding hoop piece.

Further, the turnover end of each hoop piece body is provided with an antiskid structure.

Further, each antiskid structure is a rubber layer, and each rubber layer is provided with elastic bulges.

Further, recovery sleeve holes are formed in the mounting conduit, the lower end of each recovery sleeve hole is of an opening structure, and the inner wall of each recovery sleeve hole forms an accommodating space for accommodating the anchor strap assembly; and the turnover end of each hoop piece can contract and enter the accommodating space of the corresponding recovery sleeve hole under the rotating operation of the drill rod.

Further, the inner wall of each recovery sleeve hole is a smooth concave curved surface, and each recovery sleeve hole is fixedly arranged on the outer circumferential wall of the mounting conduit and is coaxially arranged with the mounting conduit.

Further, the mounting conduit comprises a first section and a second section, the diameter of the first section is smaller than that of the second section, the first section is connected with the drill rod, and the recovery sleeve hole is arranged on the outer circumferential wall of the first section; and the second section is provided with helical clamping teeth, a threaded clamping groove is formed in the inner wall of the magnetic ring sleeve, and the helical clamping teeth are adapted to the threaded clamping groove.

Further, the recovery sleeve hole is made of an alloy material.

Further, the longitudinal cross section of the turnover end surface of each hoop piece is in a β shape with the lower part opened, the inner wall of each recovery sleeve hole is a smooth concave corrugated curved surface, and each smooth concave corrugated curved surface is adapted to the turnover end surface of the corresponding hoop piece in the β shape with the lower part opened.

Further, the turnover end surface of each hoop piece has a first turnover end surface and a second turnover end surface, and the inner surface of each hoop piece body, each second turnover end surface and each first turnover end surface are arranged in a transition manner sequentially; and each second turnover end surface is wholly of a convex structure, and each antiskid structure is arranged at the lower part of the corresponding first turnover end surface and accounts for $1/2$-$3/5$ of an area of the corresponding first turnover end surface.

In the second aspect, provided is a monitoring method for dynamic development of the overburden mining separated bed, comprising the steps of:

S1, determining a mounting depth of the settlement magnetic ring assembly based on a range of a separated bed development region;

S2, probing information of a rock stratum in a mounting depth range of the settlement magnetic ring assembly, and determining the mounting position and number of the settlement magnetic ring assembly;

S3, determining the time of the monitoring hole starting to drill based on information of coal mining footage of a working face and a drilling rate of the monitoring hole, and completing construction of the monitoring hole; and S4, mounting the settlement magnetic ring assembly at the position with a preset depth in the monitoring hole, using a layered settlement monitoring system to monitor dynamic development of the separated bed, and obtaining a rock stratum settlement amount and a development height of the separated bed.

Further, mounting the monitoring device for dynamic development of the overburden mining separated bed comprises the steps of:

S41, mounting the anchor strap assembly on the drill rod through the mounting conduit, and using the drill rod to put the settlement magnetic ring assembly in the contraction state down at the position with the preset depth in the monitoring hole;

S42, after enabling the drill rod to drop down to enable the anchor strap assembly in the contraction state to be put at the position with the preset depth, lifting up the drill rod to drive the mounting conduit to move upwards to expand the anchor strap assembly, and embedding the long wall anchoring claws into the hole walls of rocks; and S43, reversely rotating the drill rod to separate the mounting conduit from the settlement magnetic ring assembly, and repeating the above steps for mounting of the settlement magnetic ring assembly at a next position with a designed depth until mounting of the settlement magnetic ring assemblies at the positions with all designed depths are completed.

Further, if the monitoring hole is not drilled into the separated bed development region, a separated bed water inrush prevention protective bed is reserved between the bottom of the monitoring hole and a top interface of a water-conducting fissure zone.

Compared with the prior art, the present invention may have one of the following beneficial effects that:

a) For the monitoring device for dynamic development of the overburden mining separated bed provided by the present invention, the settlement magnetic ring assembly employs a structure with the upper part hooped and the lower part embedded, there are at least two fixing points of the anchor strap assembly in the expansion state and the wall of the monitoring hole in a vertical direction at different heights, and the long wall anchoring claws and the hoop pieces may exert effect at the same time to enhance each other, so that the settlement magnetic ring is stably fixed at the position with an appointed depth in the monitoring hole and is prevented from moving the monitoring hole in the monitoring process, and the accuracy of the monitoring result is improved.

b) By employing the monitoring device for dynamic development of the overburden mining separated bed provided by the present invention, after monitoring is completed, the settlement magnetic ring assembly may be moved out of the monitoring drilled hole by using the mounting conduit, so that operation is convenient in the collecting process, reuse of the settlement magnetic ring assembly is achieved, the cost may be remarkably lowered, and significant economic benefit is provided.

BRIEF DESCRIPTION OF THE DRAWINGS

In order to more clearly describe the technical solutions of the embodiments of the specification or in the prior art, the accompanying drawings required to describe the embodiments or the prior art are briefly described below. Apparently, the accompanying drawings described below are only some embodiments described in the embodiments of the specification. Those ordinary skilled in the art may further obtain other accompanying drawings based on these accompanying drawings.

REFERENCE NUMERALS 1. separated bed cavity; 2. siltstone, fine sandstone and mudstone strata; 3. medium- and coarse-grained sandstone strata; 4. separated bed development region; 4-1. quaternary aeolian sand bed; 4-2. mounting range of settlement magnetic ring; 4-3. separated bed water inrush prevention protective bed; 5. water-conducting fracture region; 6. drill rod; 7. settlement magnetic ring assembly; 7-1. magnetic induction iron ring; 7-2. magnetic ring sleeve; 7-3. anchor strap assembly; 7-3-1. long wall anchoring claw; 7-3-2. hoop piece; 7-3-3. elastomer; 7-3-4. antiskid structure; 7-3-5. connecting wire; 7-3-6. threaded clamping groove; 7-3-7. pin shaft; 8. mounting conduit; 8-1. connecting threads; 8-2 recovery sleeve hole; 8-3. helical clamping teeth.

DETAILED DESCRIPTION OF THE EMBODIMENTS

In order to make objectives, technical solutions, and advantages of embodiments of this application clearer, the technical solutions in the embodiments of this application are described clearly and completely in the following with reference to accompanying drawings in the embodiments of this application. Apparently, the described embodiments are only part rather than all of the embodiments of this application. Based on the embodiments of the present application, all the other embodiments obtained by that of ordinary skill in the art without inventive effort are within the scope of the present application.

For ease of understanding the embodiments of this application, further explanation and description will be made by the specific embodiments in conjunction with the accompanying drawings, and the embodiments do not to limit the embodiments of this application.

Figure 1:
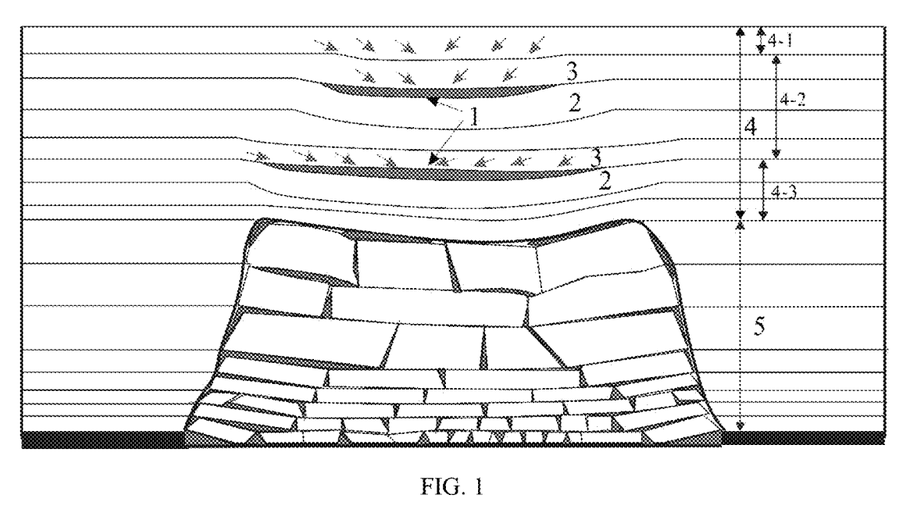
FIG. 1 is a structural schematic diagram of separated bed development caused by coal mining in the embodiment.

As stress of primary rocks of overburden is destroyed due to coal mining, a water-conducting fracture region 5 and a separated bed development region 4 may be formed in an overburden of a coal bed, as shown in FIG. 1. As there are differences in lithology of overlying strata of the water-conducting fracture region 5, hardnesses of strata with different lithology are also different. Generally, if the hardness of a sandstone stratum is large, the hardnesses of siltstone, fine sandstone and mudstone strata are small; and due to strength differences among stratum combinations of medium- and coarse-grained sandstone strata 3 (hard rocks) and the siltstone, fine sandstone and mudstone strata 2 (soft rocks) on the water-conducting fracture region 5, a separated bed cavity 1 may be formed in an interface of a hard rock stratum and a soft rock stratum in the separated bed development region 4 with coal mining. On one hand, under the effect of negative pressure, a great quantity of water resources in a water-bearing stratum of the overburden accumulate into the separated bed cavity 1; and when the scale develops to a certain degree, an instantaneous separated bed water inrush accident may happen to threaten safety mining of a working face of a mine. On the other hand, closing of the separated bed space cavity 1 of the overburden may cause ground depression to form a settling pit with ponding, and the surface soil environment is changed to threaten the surface ecology and the stability of a building.

Embodiment 1

One specific embodiment of the present invention discloses a monitoring device for dynamic development of an overburden mining separated bed, as shown in FIGS. 2-5. The monitoring device for dynamic development of the overburden mining separated bed comprises a settlement magnetic ring assembly 7 and a mounting conduit 8, wherein the settlement magnetic ring assembly 7 is mounted on a drill rod 6 of a drill rig through the monitoring conduit 8, and an anchor strap assembly 7-3 contracts and expands by using rotation, lifting and dropping of the drill rod 6 by matching with the mounting conduit 8, so that mounting and recovery of the settlement magnetic ring assembly 7 are achieved, and the defect that a settlement magnetic ring cannot be recovered without damages after monitoring is completed in the existing monitoring method is overcome.

The settlement magnetic ring assembly 7 comprises a magnetic induction iron ring 7-1, a magnetic ring sleeve 7-2 and the anchor strap assembly 7-3; the magnetic ring sleeve 7-2 is sleeved outside the magnetic induction iron ring 7-1; the anchor strap assembly 7-3 is fixedly arranged at the outer circumference of the magnetic ring sleeve 7-2 and has a contraction state and an expansion state; in the contraction state, the whole size of the anchor strap assembly 7-3 is smaller than or equal to the aperture of the monitoring hole, so that the anchor strap assembly 7-3 may move up and down in the monitoring hole; in addition, the anchor strap assembly 7-3 has the recovery elasticity of turning the contraction state to the expansion state; in the expansion state, the size of the anchor strap assembly 7-3 is larger than the aperture of the monitoring hole, there are at least two fixing points of the anchor strap assembly 7-3 and the wall of the monitoring hole in a vertical direction at different heights, and the fixing points at various heights are substantially located on the same circumference, that is, there are at least two supporting points at different heights on the wall of the monitoring hole for the anchor strap assembly 7-3 in the vertical direction, and the fixing points at various heights are substantially located on the same circumference, so that sufficient supporting reacting force exists between the anchor strap assembly 7-3 in the expansion state and the wall of the monitoring hole to ensure the mounting stability of the anchor strap assembly 7-3 and prevent movement of the settlement magnetic ring.

Figure 2:
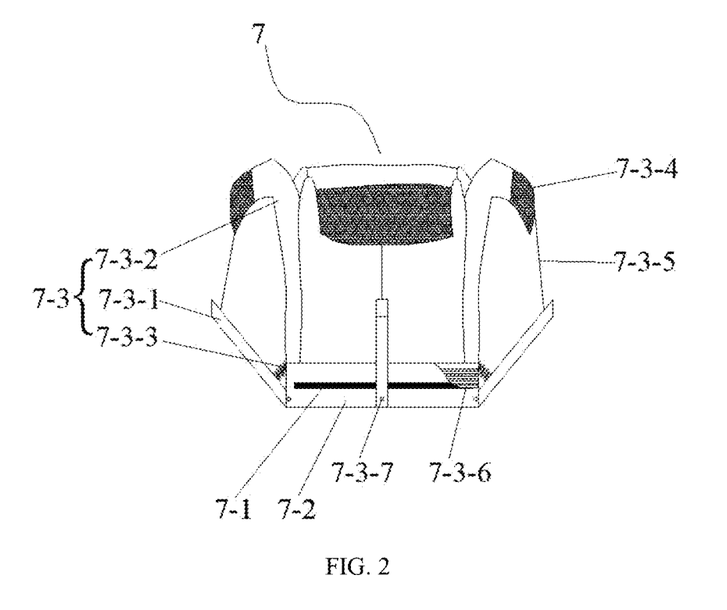
FIG. 2 is a structural schematic diagram of a settlement magnetic ring assembly of a first monitoring device for dynamic development of an overburden mining separated bed in the embodiment.
Figure 4:
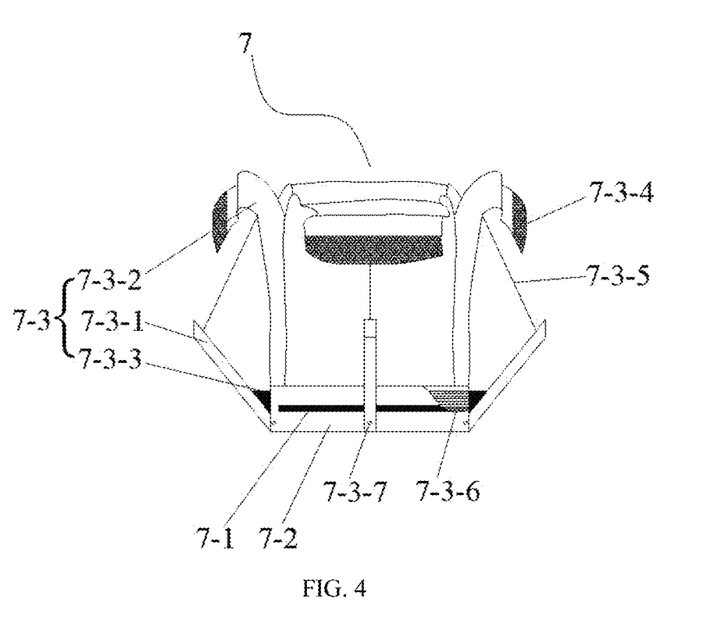
FIG. 4 is a structural schematic diagram of a settlement magnetic ring assembly of a second monitoring device for dynamic development of an overburden mining separated bed in the embodiment.

In the embodiment, the magnetic induction iron ring 7-1 is a magnetic ring, the magnetic ring has a magnetic material or a magnetic core, the magnetic ring sleeve 7-2 is of a hollow annular structure, the magnetic induction iron ring 7-1 is arranged in an internal space of the magnetic ring sleeve 7-2, inside threads are formed in the inner circumferential wall of the magnetic ring sleeve 7-2, and the anchor strap assembly 7-3 is mounted on the outer circumferential wall of the magnetic ring sleeve 7-2. Alternatively, the magnetic induction iron ring 7-1 comprises a hollow annular shell, the magnetic material or the magnetic core is arranged in the internal space of the shell, and the shell and the magnetic ring sleeve 7-2 are both a hollow iron ring which cannot influence magnetic signals.

Particularly, as shown in FIG. 2 and FIG. 4, the anchor strap assembly 7-3 comprises long wall anchoring claws 7-3-1, hoop pieces 7-3-2 and elastomers.

Each long wall anchoring claw 7-3-1 comprises a long wall rod, the first end of each long wall rod is a connecting end, each connecting end is rotationally connected to the outer circumference of the lower end of the magnetic ring sleeve 7-2, and the connecting end of each long wall anchoring claw 7-3-1 is connected to the lower circumference of the magnetic ring sleeve 7-2 through a pin shaft 7-3-7 and may rotate up and down around the pin shaft 7-3-7 in the vertical direction; the second send of each long wall rod is a claw end, and each claw end is a free end for being embedded into the wall of the monitoring hole; and the amount of the long wall anchoring claws 7-3-1 is at least two, and the plurality of connecting ends are uniformly distributed at the outer circumference of the lower end of the magnetic ring sleeve 7-2.

Hoop pieces 7-3-2, corresponding to the long wall anchoring claws 7-3-1, are arranged at the outer circumference of the upper end of the magnetic ring sleeve 7-2, that is the long wall anchoring claws 7-3-1 and the hoop pieces 7-3-2 are arranged in groups, the number of the hoop pieces 7-3-2 is at least two identical to that of the long wall anchoring claws 7-3-1, the hoop pieces 7-3-2 are uniformly distributed at the outer circumference of the upper end of the magnetic ring sleeve 7-2, and the hoop pieces 7-3-2 and the long wall anchoring claws 7-3-1 are arranged in a manner of one-to-one correspondence and are in group; and each hoop piece 7-3-2 comprises a hoop piece body, the lower end of each hoop piece body is fixed to the magnetic ring sleeve 7-2, the upper end of each hoop piece body turned over outwards in a shape of a horn mouth, and each hoop piece 7-3-2 is made of elastic steel and has certain elastic deformation ability.

Each hoop piece body is of an arch-shaped sheet structure, exemplarily, the amount of the hoop pieces 7-3-2 is four, the lower ends of the hoop pieces 7-3-2 are uniformly welded to the outer circumference of the magnetic ring sleeve 7-2, the lower parts of the four hoop piece bodies are wholly located on a same cylindrical circumference to be capable of form a hollow cylindrical structure, the diameter of the circumference of the hollow cylindrical structure is larger than or equal to that of the outer circumference of the magnetic ring sleeve 7-2.

Each long wall anchoring claw 7-3-1 is rotationally connected to the lower circumference of the magnetic ring sleeve 7-2 through a shaft, that is, and a fan-shaped rotation space is formed between each long wall anchoring claw 7-3-1 and the hoop piece body of the corresponding hoop piece 7-3-2 and is internally provided with the elastomer 7-3-3; and in the changing process of the anchor strap assembly 7-3 from the contraction state to the expansion state, each elastomer 7-3-3 may apply elastic force, enabling the corresponding long wall anchoring claw 7-3-1 to swing towards the wall of the monitoring hole, to the corresponding long wall anchoring claw 7-3-1. In the mounting process, when the settlement magnetic ring assembly 7 moves downwards along the wall of the monitoring hole, and the claw ends of the long wall anchoring claws 7-3-1 rotate towards the corresponding hoop piece bodies, the anchor strap assembly 7-3 is in the contraction state; in the presence of the elastomers, in the process that the claw ends of the long wall anchoring claws 7-3-1 rotate to approach the corresponding hoop pieces 7-3-2, the elastomers 7-3-3 are extruded and deform and have the recovery elasticity of enabling the claw ends of the long wall anchoring claws 7-3-1 to rotate away from the corresponding hoop pieces 7-3-2; and when the settlement magnetic ring assembly 7 reaches an appointed position, the drill rod 6 is lifted up to enable the settlement magnetic ring assembly 7 to move upwards, and under the effect of the recovery elasticity of the elastomers, the claw ends of the long wall anchoring claws 7-3-1 rotate away from the corresponding hoop pieces 7-3-2 and are embedded into the wall of the monitoring hole.

The turnover end of each hoop piece 7-3-2 is connected with the claw end of the corresponding long wall anchoring claw 7-3-1 through a connecting wire 7-3-5; when the claw end of each long wall anchoring claw 7-3-1 rotates away from the corresponding hoop pieces 7-3-2, the connecting wire 7-3-5 may drive the turnover end of each hoop piece 7-3-2 to turned outwards, so that the horn mouth of each hoop piece 7-3-2 is turned outwards, and an opening range is enlarged; the opened horn mouth of each hoop piece 7-3-2 is closely abutted against the wall of the monitoring hole, and the supporting diameter of the horn mouth of each hoop piece 7-3-2 becomes larger under the driving of the connecting wire 7-3-5, so that extrusion force of each hoop piece 7-3-2 to the wall of the monitoring hole is strengthened to ensure the fastening effect; and meanwhile, the claw end of each long wall anchoring claw 7-3-1 can be promoted to be embedded into the wall of the monitoring hole, contact force of the turnover end of each hoop piece 7-3-2 and the claw end of each long wall anchoring claw 7-3-1 to the wall of the monitoring hole is strengthened at the same time, and the stabilization effect is better.

In the embodiment, each elastomer 7-3-3 is one or a combination of two of the elastic rubber ring and the limiting spring.

In an alternative implementation of the embodiment, each elastomer 7-3-3 is the elastic rubber ring, each elastic rubber ring is at least partially sleeved on the outer circumference of the upper part of the magnetic ring sleeve 7-2 and may also wrap the lower part of the corresponding hoop piece body at the same time, and the inside diameter of each elastic rubber ring is smaller than or equal to the outside diameter of the magnetic ring sleeve 7-2. Further, the thickness of the wall of each elastic rubber ring gradually becomes larger in a direction from the lower end to the upper end of the magnetic ring sleeve 7-2, that is, the outside diameter of the lower part of each elastic rubber ring is smaller than that of the upper part, and the cross section of the wall of each elastic rubber ring is in a shape of an inverted triangle. With such structure arrangement, sufficient recovery elasticity of each elastic rubber ring can be ensured, and each elastic rubber ring can contract at a small angle when being mounted into the monitoring hole, so that the magnetic ring is successfully mounted in place.

In an alternative implementation of the embodiment, each elastomer 7-3-3 is the limiting spring, each group of the long wall anchoring claw 7-3-1 and the hoop piece 7-3-2 is equipped with at least one limiting spring in a matching manner, the first end of each limiting spring is connected to the long wall rod of the corresponding long wall anchoring claw 7-3-1, the second end of each limiting spring is connected to the outer circumference of the upper part of the magnetic ring sleeve 7-2, or the second end of each limiting spring is connected to the lower part of the corresponding hoop piece body. In the natural state, the diameter of a circumference, at which the claw end of each long wall anchoring claw 7-3-1 is located, is larger than the aperture of the monitoring hole; and in the process that the settlement magnetic ring is mounted in the monitoring hole, the claw end of each long wall anchoring claw 7-3-1 contracts to compress the corresponding limiting spring, and each limiting spring has the recovery elasticity of enabling the claw end of each long wall anchoring claw 7-3-1 to rotate away from the corresponding hoop piece 7-3-2.

In an alternative implementation of the embodiment, each elastomer 7-3-3 is of a combination structure of the limiting spring and the elastic rubber ring. Particularly, each group of the long wall anchoring claw 7-3-1 and the hoop piece 7-3-2 is equipped with the limiting spring and the elastic rubber ring in the matching manner, wherein each elastic rubber ring is at least partially sleeved on the outer circumference of the upper part of the magnetic ring sleeve 7-2, the first end of each limiting spring is connected to the long wall rod of the corresponding long wall anchoring claw 7-3-1, the second end of each limiting spring is connected to the lower part of the corresponding hoop piece body, a rubber ring mounting space is formed among each long wall rod, each hoop piece body, each limiting spring and the magnetic ring sleeve 7-2, and each elastic rubber ring is located in the corresponding rubber ring mounting space. With such structure arrangement, each elastic rubber ring and each limiting spring exert the effect at the same time, so that the expansion elastic force of the claw end of each long wall anchoring claw 7-3-1 is improved, the situation that expansion of the claw end of each long wall anchoring claw 7-3-1 is in failure as single elastic rubber ring or limiting spring goes wrong can be avoided, and the working reliability of the device is improved.

In the embodiment, each hoop piece 7-3-2 is made of elastic steel, and an antiskid structure is arranged at the turnover end of each hoop piece 7-3-2. After the turnover end of each hoop piece 7-3-2 expands, each antiskid structure is in friction contact to the wall of the monitoring hole; and by improving frictional force between the turnover end of each hoop piece 7-3-2 and the wall of the monitoring hole, accurate positioning of the settlement magnetic ring is facilitated, and the stability of the settlement magnetic ring is improved.

In an alternative implementation of the embodiment, each antiskid structure 7-3-4 is a rubber layer, each rubber layer is arranged at the turnover end of the corresponding hoop piece 7-3-2, and the frictional force between the turnover end of each hoop piece 7-3-2 and the wall of the monitoring hole is improved by arranging each antiskid structure.

Moreover, elastic bulges are formed on each rubber layer, and the antiskid performance is further improved by arranging the elastic bulges.

In an alternative implementation of the embodiment, the amount of the long wall anchoring claws 7-3-1 is 3-6, the long wall anchoring claws 7-3-1 are uniformly arranged at the periphery of the settlement magnetic ring, and preferably, 4 long wall anchoring claws 7-3-1 are employed.

In the embodiment, the settlement magnetic ring assembly 7 is mounted on the drill rod 6 through the mounting conduit 8. Particularly, threaded sections are arranged at both two ends of the mounting conduit 8, the first end is in threaded connection with the drill rod 6, and the second end is in threaded connection with the shell of the settlement magnetic ring assembly 7. Helical clamping teeth 8-3 formed at the lower part of the mounting conduit 8 are matched with a threaded clamping groove 7-3-6 formed in the settlement magnetic ring assembly 7, and forward rotation and reverse rotation of the drill rod 6 drive the helical clamping teeth 8-3 to be screwed into and out of the threaded clamping groove 7-3-6. Stipulated that, during forward (clockwise) rotation, the helical clamping teeth 8-3 are screwed into the threaded clamping groove 7-3-6, at this time, the mounting conduit 8 is connected with the settlement magnetic ring assembly 7; and during reverse (clockwise) rotation, the helical clamping teeth 8-3 are screwed out of the threaded clamping groove 7-3-6, at this time, the mounting conduit 8 is separated from the settlement magnetic ring assembly 7, so that connection and separation between the mounting conduit 8 and the settlement magnetic ring assembly 7 are achieved, and then recovery of the settlement magnetic ring assembly 7 without damages is achieved.

Figure 3:
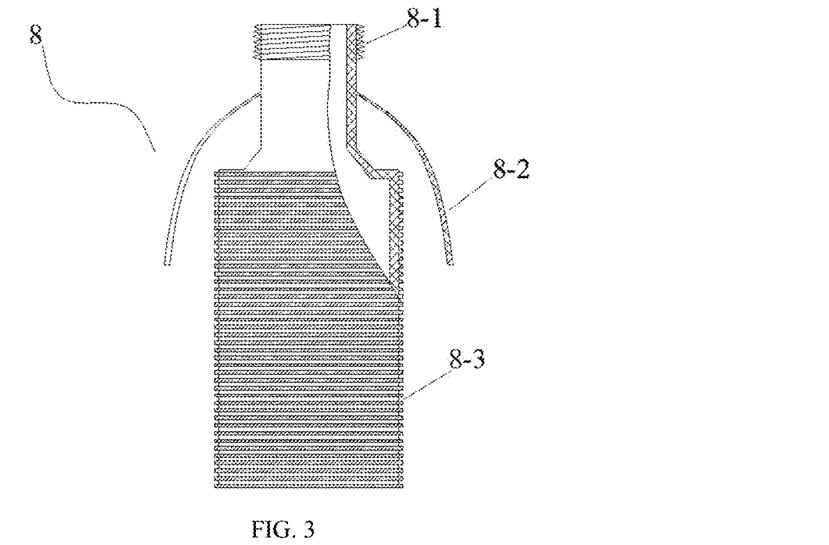
FIG. 3 is a structural schematic diagram of a mounting conduit of a first monitoring device for dynamic development of an overburden mining separated bed in the embodiment.
Figure 5:
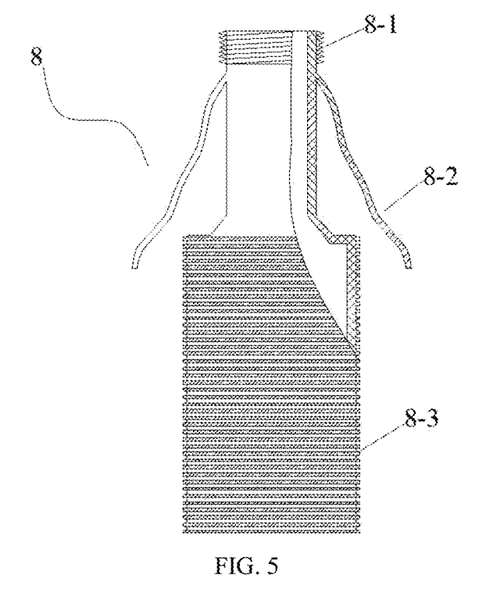
FIG. 5 is a structural schematic diagram of a mounting conduit of a second monitoring device for dynamic development of an overburden mining separated bed in the embodiment.

Particularly, as shown in FIG. 3 and FIG. 5, the mounting conduit 8 comprises a first section and a second section, the diameter of the first section is smaller than that of the second section, and the first section is in threaded connection with the drill rod 6 used by the drill rig. As the helical clamping teeth 8-3 formed at the second section is not in close contact to the threaded clamping groove 7-3-6, when the drill rod 6 rotates forwards or reversely, the second section cannot transfer force, and then threaded connection of the first section cannot be disconnected. Connection threads 8-1 are formed in one end of the first section and are matched with the threads of the drill rod 6; the other end of the first section is connected with the second section, the helical clamping teeth 8-3 are formed on the second section, the threaded clamping groove 7-3-6 is formed in the inner wall of the magnetic ring sleeve 7-2, the helical clamping teeth 8-3 are adapted to the threaded clamping groove 7-3-6, and the settlement magnetic ring assembly 7 is in threaded connection with the second section of the mounting conduit 8.

In order to achieve recovery of the settlement magnetic ring, recovery sleeve holes 8-2 are formed in the first section, the longitudinal cross section of each recovery sleeve hole 8-2 is of an Y-shaped hollow structure with large diameter of the lower end and small diameter of the upper end, the upper end of each recovery sleeve hole 8-2 is fixed to the outer circumferential wall of the first section, the lower end of each recovery sleeve hole 8-2 is of an opening structure, the inner wall of each recovery sleeve hole 8-2 is a smooth concave curved surface, and each smooth concave curved surface forms an accommodating space for accommodating the corresponding anchor strap assembly 7-3, as shown in FIG. 2 and FIG. 3.

Further, each antiskid structure 7-3-4 is arranged at the lower part of the turnover end of the corresponding hoop piece 7-3-2, an arc surface, on which the highest point of the turnover end of each hoop piece 7-3-2 is located, is a smooth upward protruding curved surface. With such structure arrangement, when the settlement magnetic ring assembly 7 is recovered, each antiskid structure 7-3-4 is not in contact to the inner wall of the corresponding recovery sleeve hole 8-2, so that the recovery resistance is weakened to achieve successful recovery of the device.

Further, as shown in FIG. 4 and FIG. 5, the longitudinal cross section of the turnover end surface of each hoop piece 7-3-2 is approximately in a β shape, the lower part of the turnover end surface of each β-shaped structure is opened, the inner wall of each recovery sleeve hole 8-2 is a smooth concave corrugated curved surface, and each smooth concave corrugated curved surface is adapted to the turnover end surface of the corresponding β-shaped hoop piece 7-3-2 and forms an accommodating space for accommodating the anchor strap assembly 7-3. That is, the turnover end surface of each hoop piece 7-3-2 has a first turnover end surface and a second turnover end surface which are arranged in a transition manner, and the inner surface of each hoop piece body, each second turnover end surface and each first turnover end surface are connected with each other sequentially, wherein the inner surface of each hoop piece body refers to the surface, facing away from the wall of the monitoring hole, each second turnover end surface is wholly of a convex structure, each convex second turnover end surface is located between the inner surface of each hoop piece body and each first turnover end surface, at least a part of each first turnover end surface faces the wall of the monitoring hole, each antiskid structure is arranged on the corresponding first turnover end surface, located at the lower part of the corresponding first turnover end surface and accounts for ½-⅗ of an area of the corresponding first turnover end surface, and the upper part of each first turnover end surface and each second turnover end surface are smooth curved surfaces. When the settlement magnetic ring assembly 7 is recovered, each smooth second turnover end surface of the convex structure is in contact to the smooth surface of the inner wall of the corresponding recovery sleeve hole 8-2, and each recovery sleeve hole 8-2 is not in contact to the corresponding antiskid structure, so that the recovery resistance is weakened to achieve successful recovery of the device. One end of each connecting wire 7-3-5 is connected to the corresponding second turnover end surface, and the other end is connected to the long wall rod of the corresponding first turnover end surface; and when each connecting wire drives the corresponding turnover end to open, each antiskid structure is made to be in contact to the wall of the monitoring hole by needing to pull the turnover end at a small distance only, so that the accuracy of the mounting position is improved, and the working reliability of the device is ensured.

When the settlement magnetic ring is recovered, and the drill rod 6 is put down to reach the position of the magnetic ring, the drill rod 6 is rotated forwards to drive the mounting conduit 8 to be screwed into the settlement magnetic ring assembly 7, the settlement magnetic ring assembly 7 moves upwards along the second section of the mounting conduit 8, the second turnover end surfaces of the horn mount shaped turnover ends at the upper ends of the hoop piece bodies firstly enter the accommodating spaces of the recovery sleeve holes 8-2 respectively to be in contact to the smooth concave corrugated curved surfaces of the recovery sleeve holes 8-2 respectively, the first turnover end surfaces are not in contact to the inner wall surfaces of the recovery sleeve holes 8-2 respectively and are continuously screwed along with the drill rod 6, and the settlement magnetic ring assembly 7 continuously moves along the helical clamping teeth 8-3 of the second section. Under the limitation of the smooth concave corrugated curved surfaces, the second turnover end surfaces contract and get closer to the center line of the settlement magnetic ring assembly 7 from the interiors of the recovery sleeve holes 8-2, and then the connecting wires 7-3-5 are driven to lift the claw ends of the corresponding long wall anchoring claws 7-3-1 upwards, so that the claw ends of the long wall anchoring claws 7-3-1 rotate towards the corresponding hoop pieces 7-3-2 and are departed from the wall of the monitoring hole, and recovery of the settlement magnetic ring assembly 7 is achieved.

In order to prevent deformation of each recovery sleeve hole 8-2, each recovery sleeve hole 8-2 is made of an alloy material and has high hardness and abrasion resistance; and alternatively, each recovery sleeve hole 8-2 is wholly formed by forging and machining a steel plate with a thickness being 5 mm.

In order to enable the helical clamping teeth 8-3 to be successfully screwed into or out of the threaded clamping groove 7-3-6 in the mounting process and prevent the mounting conduit 8 from dropping off from the drill rod 6, the width of the threaded clamping groove 7-3-6 is larger than that of the helical clamping teeth 8-3; and alternatively, the width of the threaded clamping groove 7-3-6 is 0.2 mm, and the width of the helical clamping teeth 8-3 is 0.1 mm, so that the helical clamping teeth 8-3 cannot transfer torsion to the upper part.

The embodiment further discloses a mounting operation method of the monitoring device for dynamic development of the overburden mining separated bed, particularly comprising the following steps that:

step 1, the anchor strap assembly 7-3 is mounted on the drill rod 6 through the mounting conduit 8, the drill rod 6 drops to enable the anchor strap assembly 7-3 to be put down into a mouth of the monitoring hole, the anchor strap assembly 7-3 is set into the contraction state and extends into the monitoring hole, and the anchor strap assembly 7-3 in the contraction state is put down to a position with a preset depth in the monitoring hole.

Figure 6:
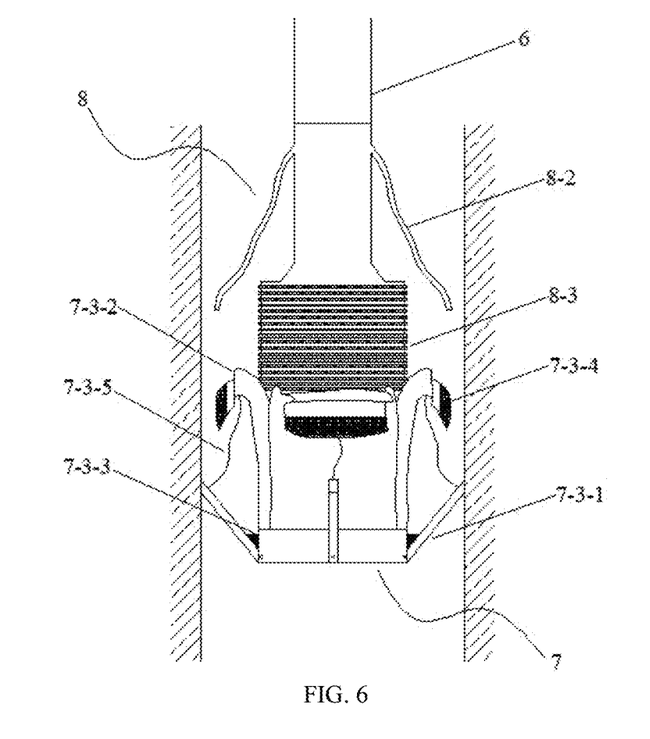
FIG. 6 is a schematic diagram of a monitoring device for dynamic development of an overburden mining separated bed in a putting-down state in the embodiment.

The mounting conduit 8 is connected with the drill rod 6 through the connection threads 8-1 on the ground, and the settlement magnetic ring assembly 7 is manually screwed into the threaded clamping groove 7-3-6 through the helical clamping teeth 8-3 so as to be connected to the lower part of the mounting conduit 8; and the drill rig descends the drill rod 6 to put down the settlement magnetic ring assembly 7 into the monitoring hole, the anchor strap assembly 7-3 is made into the contraction state manually or by using the mouth of the monitoring hole, that is, in the process of putting down the settlement magnetic ring assembly 7, the long wall anchoring claws 7-3-1 cling to the hole wall to enable the elastomers 7-3-3 to be in the compressed state, and at this time, the connecting wires 7-3-5 are in a loose state, as shown in FIG. 6.

Step 2, after the drill rod 6 drops down to enable the anchor strap assembly 7 in the contraction state to be put at the position with the preset depth, the drill rod 6 is lifted up to drive the mounting conduit 8 to move upwards to expand the anchor strap assembly 7-3, and the long wall anchoring claws 7-3-1 are stably embedded into the hole walls of rocks after the anchor strap assembly 7-3 expands.

Figure 7:
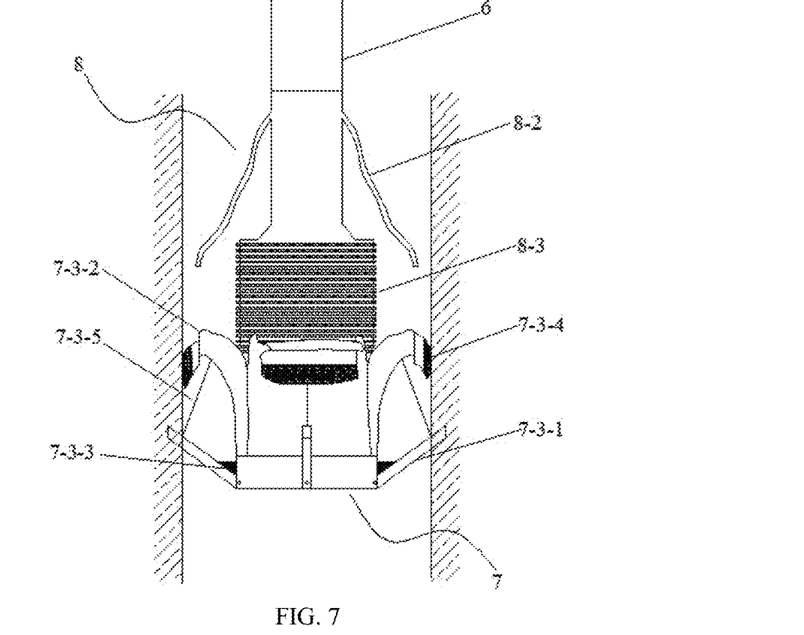
FIG. 7 is a schematic diagram of a monitoring device for dynamic development of an overburden mining separated bed in a state of being embedded into hole walls in the embodiment.

Particularly, according to the designed position of the settlement magnetic ring, after the settlement magnetic ring assembly 7 is put down to the designed position by using the drill rod 6, the drill rig lifts up the drill rod 6 to drive the mounting conduit 8 to enable the settlement magnetic ring assembly 7 to move upwards; as the long wall anchoring claws 7-3-1 are in an outward opening state through the compressed elastomers 7-3-3, and the claw ends of the long wall anchoring claws 7-3-1 are sharpened, in the lifting process of the drill rod 6, the long wall anchoring claws 7-3-1 may be stably embedded into the hole walls of rocks; meanwhile, the hoop pieces 7-3-2 are driven by downward rotation of the long wall anchoring claws 7-3-1 around the pin shafts 7-3-7 to be turned over towards the periphery in a horn mouth shape, and the antiskid structures 7-3-4 at the end parts of the hoop pieces 7-3-2 may be in contact to the hole wall as the opening ranges of the hoop pieces 7-3-2 are enlarged; and under the effect of friction of the antiskid structures 7-3-4, the hoop pieces 7-3-2 may be further turned over, and finally, the upper end of the settlement magnetic ring is stably fixed to the wall of the monitoring hole, as shown in FIG. 7.

When the drill rod 6 is lifted up, the long wall anchoring claws 7-3-1 at the lower end of the settlement magnetic ring assembly 7 and the hoop pieces 7-3-2 at the upper end of the settlement magnetic ring assembly 7 exert the effect at the same time through the connecting wires 7-3-5 to enhance each other, that is, the deeper the long wall anchoring claws 7-3-1 at the lower end embedded into the hole wall is, the stronger the extraction acting force, applied to the wall of the monitoring hole, of the hoop pieces 7-3-2 is, and finally, the settlement magnetic ring is stably fixed to the hole wall.

Step 3, the drill rod 6 is reversely rotated to enable the mounting conduit 8 to be separated from the settlement magnetic ring assembly 7, and the above steps are repeated for mounting of the settlement magnetic ring assembly 7 at a next position with a designed depth until mounting of the settlement magnetic ring assemblies at the positions with all designed depths are completed.

After the settlement magnetic ring is fixed to the hole wall, lifting of the drill rod 6 is blocked, and then a drill rig pressure gauge is observed; and when a change in the pressure gauge is relatively large, stated that mounting succeeds, and at this time, the drill rod 6 is reversely rotated to enable the helical clamping teeth 8-3 to be screwed out of the threaded clamping groove 7-3-6 to enable the mounting conduit 8 to be separated from the settlement magnetic ring assembly 7. The settlement magnetic rings with the designed amount (for example, 60) may be sequentially mounted from bottom to top according to the method.

Figure 8:
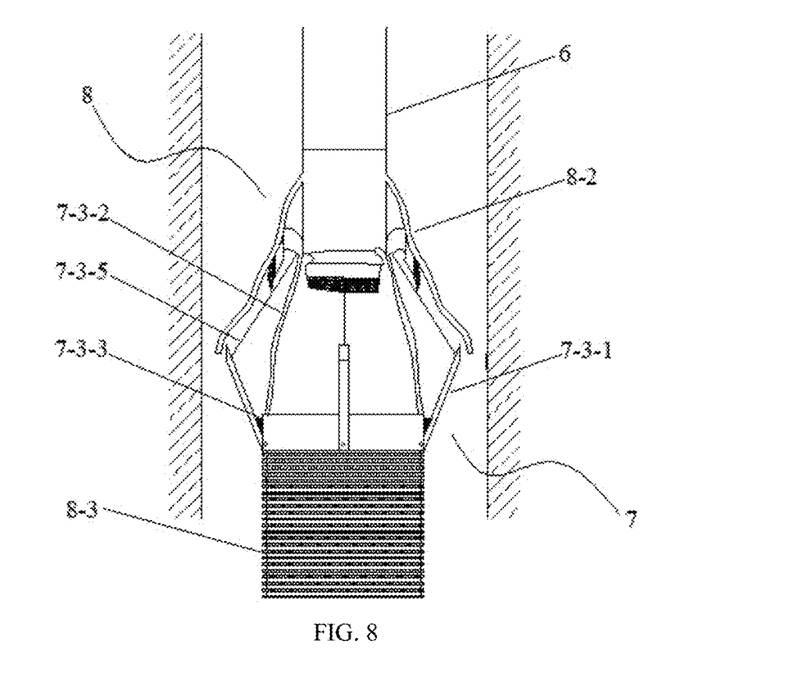
FIG. 8 is a schematic diagram of a monitoring device for dynamic development of an overburden mining separated bed in a recovery state in the embodiment.

After monitoring of dynamic develop of the separated bed is completed, the drill rig descends the drill rod 6 and the mounting conduit 8; and after the mounting conduit 8 reaches the position of the settlement magnetic ring assembly 7, the drill rod 6 is rotated forwards to drive the mounting conduit 8 to rotate so as to enable the helical clamping teeth 8-3 to be screwed into the threaded clamping groove 7-3-6. As shown in FIG. 8, in the screwing-in process, due to the Y-shaped structure design with a large diameter of the lower end and a small diameter of the upper end of each recovery sleeve hole 8-2, each hoop piece 7-3-2 may enter the corresponding recovery sleeve hole 8-2 and is turned inwards in the corresponding recovery sleeve hole 8-2 with further rotation of the drill rod 6, then each connecting wire 7-3-5 is driven to lift the corresponding long wall anchoring claw 7-3-1 upwards, and then each long wall anchoring claw 7-3-1 rotates upwards to be departed from the hole wall to achieve recovery of the settlement magnetic ring assembly 7. The 60 magnetic rings may be sequentially recovered without damages from top to bottom according to the method.

The embodiment further provides a layered settlement monitoring system which comprises the monitoring device for dynamic development of the overburden mining separated bed of the embodiment and a settlement monitor.

Compared with the prior art, the monitoring device for dynamic development of the overburden mining separated bed provided by the embodiment at least has one of the following beneficial effects that:

1. The settlement magnetic ring assembly with an innovative design is of a simple structure; the settlement magnetic rings are successfully applied to layered monitoring of a rock stratum from soil layer monitoring, the principle is simple, operation is convenient and labor-saving, and the dynamic development process of the separated bed can be simply, effectively and accurately monitored, so that the strong evidence is provided to determination of a development position and the size of a development space of the separated bed, which has an important significance in safety mining of coals and ground grouting for settlement prevention.

2. The settlement magnetic ring assembly employs a structure with the upper part hooped and the lower part embedded, the long wall anchoring claws and the hoop pieces may exert the effect at the same time to enhance each other, so that the settlement magnetic ring is stably fixed to the wall of the monitoring hole, and the accuracy of monitoring dynamic development of separated bed is improved; and moreover, after mounting is completed, the settlement magnetic ring assembly can be moved out of the drilled hole by using the mounting conduit, so that operation is convenient in the collecting process, reuse of the settlement magnetic ring assembly is achieved, the cost can be remarkably lowered, and significant economic benefit is provided.

3. The inner wall of each recovery sleeve hole is a smooth concave corrugated curved surface, and each smooth concave corrugated curved surface is adapted to the turnover end surface of the corresponding hoop piece approximately in the β shape and forms the accommodating space; and when the settlement magnetic ring assembly is recovered, each smooth second turnover end surface of the convex structure is in contact to the smooth surface of the inner wall of the corresponding recovery sleeve hole, and each recovery sleeve hole is not in contact to the corresponding antiskid structure, so that the recovery resistance is weakened to achieve successful recovery of the device.

4. By mounting the settlement magnetic ring assembly with the mounting conduit, the defect that the magnetic ring is easily blocked by soil grains when the magnetic ring is mounted by using the settlement pipe traditionally can be avoided, and the working stability of the monitoring device is remarkably improved.

Embodiment 2

Another specific embodiment of the present invention discloses a monitoring method for dynamic development of an overburden mining separated bed, using the monitoring device for dynamic development of the overburden mining separated bed provided by the embodiment to monitor dynamic development of the separated bed.

Compared with the prior art, the beneficial effects of the monitoring method for dynamic development of the overburden mining separated bed provided by the embodiment are substantially the same as those of the monitoring device for dynamic development of the overburden mining separated bed provided by the Embodiment 1, which is not elaborated here.

The monitoring method for dynamic development of the overburden mining separated bed comprises the following steps that:

S1, a mounting depth of the settlement magnetic ring assembly 7 is determined based on a range of a separated bed development region 4.

As stress of primary rocks of overburden is destroyed due to coal mining, a water-conducting fracture region 5 and a separated bed development region 4 are formed in an overburden of a coal bed, a range of the separated bed development region 4 is from the bottom interface of a quaternary aeolian sand bed 4-1 (that is, quaternary soil layer) to the top interface of a water-conducting fissure zone, and the development depth $H_s$ of separated bed is calculated according to a following formula:

$$H_s = H_c - H_f$$

In the formula, $H_s$ is the development depth of separated bed, m; $H_c$ is a buried depth of a roof of the coal bed, m; and $H_f$ is a development height of the water-conducting zone, m.

A calculation formula of the development height $H_f$ of the water-conducting zone is as follows:

$$H_f = C \times M_c$$

In the formula, $M_c$ is a cumulative mining thickness of the coal bed, m; and C is a ratio of a height of a fractured zone to a mining height.

Or the development height $H_f$ of the water-conducting zone is obtained by a test method with optical fibers, drilling fluid leakage or a borehole television.

In order to prevent separated bed water from rushing into the coal working face, a mounting range of the settlement magnetic ring is form the bottom interface of the quaternary aeolian sand bed 4-1 of the separated bed development region 4 to the top interface of a separated bed water inrush prevention protective bed, that is, during construction of the monitoring hole, the monitoring hole does not penetrate through the separated bed development region 4, a stratum with a certain thickness, which is a separated bed water inrush prevention protective bed 4-3, is reserved between the bottom of the monitoring hole and the top interface of the water-conducting zone, and the presence of the separated bed water inrush prevention protective bed 4-3 effectively prevents the separated bed water from rushing into the coal working face from the monitoring hole; and after the separated bed water inrush prevention protective bed 4-3 is left, the settlement magnetic ring assembly 7 is mounted at the quaternary aeolian sand bed 4-1 in the separated bed development region 4, and the mounting range 4-2 of the settlement magnetic ring assembly is determined. The drilling depth $H_m$ of the monitoring hole is calculated according to a following formula:

$$H_m = H_s - M_p$$

In the formula, $H_m$ is the drilling depth of the monitoring hole, m; and $M_p$ is a thickness of the separated bed water inrush prevention protective bed, m.

The thickness of the separated bed water inrush prevention protective bed is calculated according to a following formula:

$$M_P = \frac{P}{T_s}$$

In the formula, P is water pressure of a water-bearing stratum overlying a separated bed, MPa; and $T_s$ is a critical water inrush coefficient, wherein the critical water inrush coefficient takes a value according to a stipulation in *Detailed Rules of Coal Mine Water Control*, that is, the critical water inrush coefficient takes the value as 0.1 MPa/m when no construction is destroyed and takes the value as 0.06 MPa/m when a construction is destroyed.

S2, Information of a rock stratum in a mounting depth range of the settlement magnetic ring assembly 7 in the step S1 is probed, and the mounting position and amount of the settlement magnetic rings are determined.

Information, such as the lithology and the thickness of an overburden rock stratum, the position of an interface of rock strata and the position of an interface of strata, in the mounting range of the settlement magnetic rings is determined according to a method of drilling the ground for core, borehole television imaging or drilling for geophysics exploration, the settlement magnetic rings are mounted at the upper and lower positions at the interfaces of difference rock strata and the interfaces of the strata, and thus design on the mounting position and the mounting amount of the settlement magnetic rings is achieved.

S3, The time of the monitoring hole starting to drill is determined based on information of coal mining footage of a working face and a drilling rate of the monitoring hole, and construction of the monitoring hole is completed.

Considering that there are differences in settlement of the rock strata at different distances from the coal working face within a certain range due to coal mining, stratum movements mainly in horizontal and vertical directions are generated. As the coal working face is continuously advanced and approaches the position of the monitoring hole, the overburden of a coal bed adjacent to the monitoring hole may generate the stratum movement mainly in the horizontal direction and then the stratum movement mainly in the vertical direction. If after the monitoring hole is formed or the settlement monitoring device is mounted, the overburden rocks at the periphery of the monitoring hole mainly conduct horizontal movement, the overburden horizontal movement caused by coal mining may cause dislocation of the monitoring hole, and thus the monitoring device cannot be mounted, or the settlement pipe in the monitoring hole is damaged. After the monitoring hole is formed, when the coal working face is at a distance, smaller than a certain distance, from the monitoring hole, the overburden rock stratum of the coal bed mainly conducts the vertical movement with a small horizontal movement quantity, and dislocation of the monitoring hole cannot occur.

Figure 9:
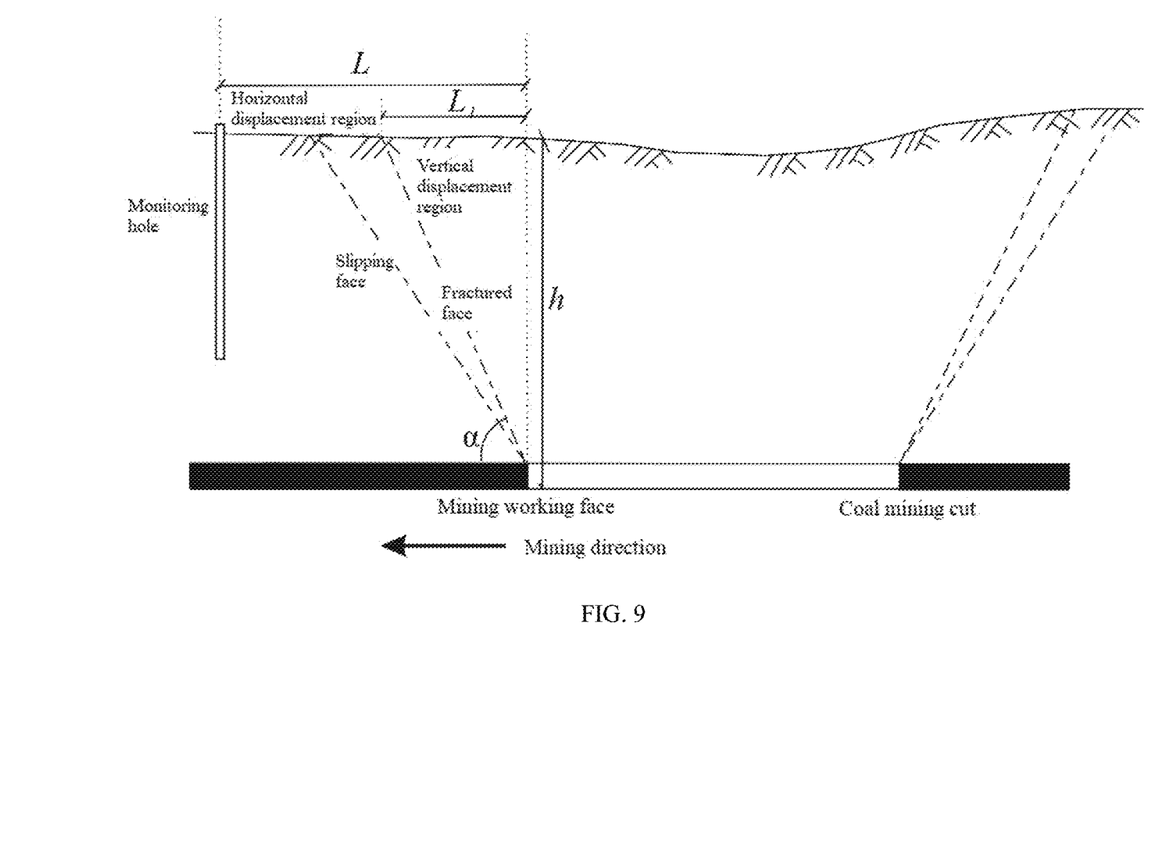
FIG. 9 is a schematic diagram of a range of an overburden vertical movement region caused by coal mining in the embodiment.

As shown in FIG. 9, when a distance L between the coal working face and the monitoring hole is smaller than $L_1$, after the monitoring hole is formed, dislocation cannot occur. A calculation formula of $L_1$ is as follows:

$$L_1 = \frac{h}{\tan \alpha}$$

In the formula, $L_1$ is a fracture influencing distance, m; h is a mining depth, m; and α is a fracture influencing angle, °.

As the coal working interface is continuously advanced forwards, in the coal mining process, the coal working interface is dynamically changing, relevant to a coal mining footage, and in addition, the depth of the monitoring hole is large, so that construction of the monitoring hole needs a certain time to be completed. In order to improve the working efficiency, forward advancing of the coal working interface and the drilling construction of the monitoring hole may be conducted at the same time, and the opportunity of starting to drill the monitoring hole and the mounting time of one settlement magnetic ring are determined according to an average daily footage and an average daily drilling depth of coal mining.

That is, if drilling of the monitoring hole and forward advancing of the coal working interface are conducted at the same time, when the monitoring hole is drilled to a preset drilling depth, a distance between a working point of coal mining equipment of a current coal working face and the monitoring hole needs to be ensured not to exceed $L_1$ at this time.

Considering that the drilling construction of the monitoring hole needs a certain time, in order to thoroughly avoid damages caused by horizontal movement of the overburden due to coal mining on the settlement pipe, in the step S3, the time of starting to drill the monitoring hole is earliest after that the distance between the coal working face and the monitoring hole is $L_1$+D; and in order to not influence settlement monitoring, the time of starting to drill the monitoring hole is latest before that the distance between the coal working face and the monitoring hole is D, wherein a calculation formula of D is as follows:

$$D = v_1 \times \frac{H_m}{v_2}$$

In the formula, D is a coal bed footage during hole drilling, m; $H_m$ is a drilling depth of the monitoring hole, m; $v_1$ is an average daily footage of coal mining, m; and $v_2$ is an average daily drilling depth, m.

S4, after construction of the monitoring hole is completed, the settlement magnetic ring assembly 7 is mounted in the monitoring hole at a position with the preset depth in the monitoring hole, a layered settlement monitoring system is used to monitor dynamic development of the separated bed, and a settlement amount and a development height of the separated bed are obtained according to monitoring data.

S41, after construction of the monitoring hole is completed, the settlement magnetic ring assembly 7 is mounted at the position with the preset depth in the monitoring hole, which comprises the following mounting steps that:

S411, the anchor strap assembly 7-3 is mounted on the drill rod 6 through the mounting conduit 8, and the drill rod 6 is used to put the settlement magnetic ring assembly 7 in the contraction state down at the position with the preset depth in the monitoring hole;

S412, after the drill rod 6 drop down to enable the anchor strap assembly 7-3 in the contraction state to be put at the position with the preset depth, the drill rod 6 is lifted up to drive the mounting conduit 8 to move upwards to expand the anchor strap assembly 7-3, and the long wall anchoring claws 7-3-1 are embedded into the hole walls of rocks; and S413, the drill rod 6 is reversely rotated to enable the mounting conduit 8 to be separated from the settlement magnetic ring assembly 7, and the above steps are repeated for mounting of the settlement magnetic ring assembly 7 at a next position with a designed depth until mounting of the settlement magnetic ring assemblies 7 at the positions with all designed depths are completed.

S42, after the settlement magnetic ring assemblies 7 are mounted at the positions with the preset depths, the settlement monitor is started to conduct settlement monitoring, and the settlement amount and the development height of the separated bed are calculated according to monitoring data, which specifically comprises the following steps that:

S421, with an initial buried depth of each measured settlement magnetic ring assembly 7 after mounting is completed as a calculation initial point, and the settlement amount is calculated according to monitoring data of the same settlement magnetic ring assembly 7, wherein a calculation formula of the settlement amount of the settlement magnetic ring is as follows:

$$S = S_1 - S_0$$

in the formula, S is the settlement amount of the settlement magnetic ring, m; $S_1$ is a buried depth of the monitored settlement magnetic ring, m; and $S_0$ is an initial buried depth of the settlement magnetic ring, m.

S422, The development height of the separated bed is further calculated according to the settlement amounts of the adjacent settlement magnetic rings, wherein a calculation formula of the development height $M_s$ of the separated bed is as follows:

$$M_s = S_{lower} - S_{upper}$$

in the formula, $M_s$ is the development height of the separated bed, m; $S_{lower}$ is the settlement amount of a lower settlement magnetic ring, m; and $S_{upper}$ is the settlement amount of an upper settlement magnetic ring, m.

S5, A relationship diagram of the development height of the separated bed and the time is drawn according to calculated data of the development height of the separated bed, the dynamic development process of the separated bed is judged, and a suitable grouting opportunity is selected based on the rule of the dynamic development process of the separated bed to prevent and control water of separated bed water inrush and ground settlement caused by coal mining for coal mine geohazard prevention and control.

A bed-separation space is formed by uneven settlement of an overlying rock stratum caused by coal mining, and closing of the bed-separation space may cause disasters, such as separated bed water inrush of the coal working face and ground settlement; the relationship diagram of development of the separated bed and the time is drawn based on the monitoring data, and the rule of dynamic development of the overburden mining separated bed is held; and the time before closing of the bed-separation space (that is when the bed-separation space develops to the largest, grouting filling is conducted in the bed-separation space) is the best time for preventing and controlling water of separated bed water inrush and ground settlement, and thus the coal mine geohazard, such as ground settlement, caused by separated bed water inrush and coal mining can be effectively prevented.

The aforementioned specific implementations make further description of the objectives, technical solutions and beneficial effects of this application in detail. It should be understood that the foregoing is only specific implementations of this application and is not intended to be limiting of the scope of this application, and any modifications, equivalent substitutions, improvements and the like within the spirit and principles of the present application are intended to be embraced by the protection range of the present application.

What is claimed is:

1. A monitoring device for dynamic development of an overburden mining separated bed, comprising:
   a settlement magnetic ring assembly, comprising an anchor strap assembly, a magnetic induction iron ring and a magnetic ring sleeve sleeved outside the magnetic induction iron ring, wherein the anchor strap assembly is arranged at an outer circumference of the magnetic ring sleeve, the anchor strap assembly has a contraction state and an expansion state, the anchor strap assembly in the contraction state is configured to move in a monitoring hole, and at least two fixing points at different heights are formed in the anchor strap assembly in the expansion state and a wall of the monitoring hole in a vertical direction; and
   a mounting conduit, wherein two ends of the mounting conduit are connected to a drill rod and the magnetic ring sleeve respectively, the anchor strap assembly is in the contraction state or the expansion state by matching the drill rod with the mounting conduit to achieve mounting and recovery of the settlement magnetic ring assembly.

2. The monitoring device according to claim 1, wherein the anchor strap assembly comprises long wall anchoring claws and hoop pieces;
   a first end of each long wall anchoring claw of the long wall anchoring claws is connected to the outer circumference of the magnetic ring sleeve through a shaft, and a second end of the each long wall anchoring claw is a claw end for a need of being embedded into the wall of the monitoring hole in the expansion state; and
   a lower end of each hoop piece of the hoop pieces is fixed to the magnetic ring sleeve, an upper end of the each hoop piece is provided with a turnover end in a shape of a horn mouth, and the turnover end is connected to the claw end of the corresponding long wall anchoring claw through a connection wire.

3. The monitoring device according to claim 2, wherein the hoop pieces and the long wall anchoring claws are arranged in groups, and a number of the hoop pieces is at least two, and the hoop pieces are uniformly arranged on an outer circumference of an upper end of the magnetic ring sleeve.

4. The monitoring device according to claim 3, wherein rotation spaces for the long wall anchoring claws to rotate around shafts are formed in outer sides of the hoop pieces respectively, and the rotation spaces are internally provided with elastomers respectively.

5. The monitoring device according to claim 4, wherein each elastomer of the elastomers is an elastic rubber ring, and the elastic rubber ring is at least partially sleeved on the magnetic ring sleeve;
   or the each elastomer is a limiting spring, wherein a first end of the limiting spring is connected to the corresponding long wall anchoring claw, and a second end of the limiting spring is connected to an outer circumference of an upper part of the magnetic ring sleeve or to a lower part of the corresponding hoop piece.

6. The monitoring device according to claim 2, wherein the turnover end of each hoop piece body is provided with an antiskid structure.

7. The monitoring device according to claim 6, wherein the antiskid structure is a rubber layer, and the rubber layer is provided with elastic bulges.

8. The monitoring device according to claim 2, wherein recovery sleeve holes are formed in the mounting conduit, a lower end of each recovery sleeve hole of the recovery sleeve holes is of an opening structure, and an inner wall of the each recovery sleeve hole forms an accommodating space for accommodating the anchor strap assembly; and
   the turnover end of the each hoop piece is configured to contract and enter the accommodating space of the corresponding recovery sleeve hole under a rotating operation of the drill rod.

9. The monitoring device according to claim 8, wherein the inner wall of the each recovery sleeve hole is a smooth concave curved surface, the each recovery sleeve hole is fixedly arranged on an outer circumferential wall of the mounting conduit, and the each recovery sleeve hole is coaxially arranged with the mounting conduit.

10. The monitoring device according to claim 9, wherein the mounting conduit comprises a first section and a second section, a diameter of the first section is smaller than a diameter of the second section, the first section is connected to the drill rod, and the each recovery sleeve hole is arranged on an outer circumferential wall of the first section; and
    the second section is provided with helical clamping teeth, a threaded clamping groove is formed in an inner wall of the magnetic ring sleeve, and the helical clamping teeth are adapted to the threaded clamping groove.

11. The monitoring device according to claim 10, wherein a width of the threaded clamping groove is 0.2 mm, and a width of the helical clamping teeth is 0.1 mm.

12. The monitoring device according to claim 9, wherein the each recovery sleeve hole is made of an alloy material.

13. The monitoring device according to claim 12, wherein a longitudinal cross section of a turnover end surface of the each hoop piece is in a beta shape with a lower part opened, the inner wall of the each recovery sleeve hole is a smooth concave corrugated curved surface, and the smooth concave corrugated curved surface is adapted to the turnover end surface of the corresponding hoop piece in the beta shape with the lower part opened.

14. The monitoring device according to claim 13, wherein the turnover end surface of the each hoop piece has a first turnover end surface and a second turnover end surface, and an inner surface of each hoop piece body, the second turnover end surface and the first turnover end surface are arranged in a transition manner sequentially; and
    the second turnover end surface is wholly of a convex structure, the antiskid structure is arranged at a lower part of the corresponding first turnover end surface, and the antiskid structure accounts for ½-⅗ of an area of the corresponding first turnover end surface.

15. A monitoring method for dynamic development of an overburden mining separated bed, used for monitoring dynamic development of a separated bed using the monitoring device of claim 1,
    comprising the steps of:
    S1, determining a mounting depth of the settlement magnetic ring assembly based on a range of a separated bed development region;
    S2, probing information of a rock stratum in a mounting depth range of the settlement magnetic ring assembly, and determining a mounting position and a number of the settlement magnetic ring assembly;
    S3, determining a time of the monitoring hole starting to drill based on information of coal mining footage of a working face and a drilling rate of the monitoring hole, and completing construction of the monitoring hole; and S4, mounting the settlement magnetic ring assembly at a position with a preset depth in the monitoring hole, using a layered settlement monitoring system to monitor the dynamic development of the separated bed, and obtaining a rock stratum settlement amount and a separated bed development height.

16. The monitoring method according to claim 15, wherein mounting the monitoring device comprises the steps of:

S41, mounting the anchor strap assembly on the drill rod through the mounting conduit, and using the drill rod to put the settlement magnetic ring assembly in the contraction state down at the position with the preset depth in the monitoring hole;

S42, after enabling the drill rod to drop down to enable the anchor strap assembly in the contraction state to be put at the position with the preset depth, lifting up the drill rod to drive the mounting conduit to move upward to expand the anchor strap assembly, and embedding the long wall anchoring claws into hole walls of rocks; and S43, reversely rotating the drill rod to separate the mounting conduit from the settlement magnetic ring assembly, and repeating S41-S43 for mounting the settlement magnetic ring assembly at a next position with a designed depth until mounting of settlement magnetic ring assemblies at positions with all designed depths is completed.

17. The monitoring method according to claim 16, wherein the range of the separated bed development region is from a bottom interface of a quaternary aeolian sand bed to a top interface of a water-conducting fissure zone, and a development depth $H_s$ of the separated bed is calculated according to a following formula:

$$H_s = H_c - H_f$$

wherein, $H_c$ is a buried depth of a roof of a coal bed, with a unit of m; $H_f$ is a development height of the water-conducting fissure zone, with a unit of m; and a calculation formula of $H_f$ is as follows:

$$H_f = C \times M_c$$

wherein, $M_c$ is a cumulative mining thickness of the coal bed, with a unit of m; and C is a ratio of a height of a fractured zone to a mining height.

18. The monitoring method according to claim 17, wherein when the monitoring hole is not drilled into the separated bed development region, a separated bed water inrush prevention protective bed is reserved between a bottom of the monitoring hole and the top interface of the water-conducting fissure zone.

19. The monitoring method according to claim 18, wherein a thickness $M_p$ of the separated bed water inrush prevention protective bed is calculated according to a following formula:

$$M_P = \frac{P}{T_s}$$

wherein, P is a water pressure of a water-bearing stratum overlying the separated bed, with a unit of MPa; and $T_s$ is a critical water inrush coefficient, with a unit of MPa/m;

a drilling depth $H_m$ of the monitoring hole is calculated according to a following formula:

$$H_m = H_s - M_p$$

wherein, $H_m$ is the drilling depth of the monitoring hole, with a unit of m; and $M_p$ is the thickness of the separated bed water inrush prevention protective bed, with a unit of m.

20. The monitoring method according to claim 19, wherein in the step S3, the time of the monitoring hole starting to drill is after that a distance between a coal working face and the monitoring hole is $L_1 + D$ and before that a distance between the coal working face and the monitoring hole is D, wherein a calculation formula of $L_1$ is as follows:

$$L_1 = \frac{h}{\tan \alpha}$$

a calculation formula of D is as follows:

$$D = v_1 \times \frac{H_m}{v_2}$$

wherein, $L_1$ is a fracture influencing distance, with a unit of m; h is a mining depth, with a unit of m; $\alpha$ is a fracture influencing angle, with a unit of °; D is a coal bed footage during hole drilling, with a unit of m; $H_m$ is the drilling depth of the monitoring hole, with a unit of m; $v_1$ is an average daily footage of coal mining, with a unit of m; and $v_2$ is an average daily drilling depth, with a unit of m.

* * * * *